(12) United States Patent
Lee et al.

(10) Patent No.: US 11,020,729 B1
(45) Date of Patent: Jun. 1, 2021

(54) HETEROATOM LIGAND, OLIGOMERIZATION CATALYST CONTAINING SAME, AND METHOD FOR PREPARING OLIGOMER

(71) Applicants: SK Innovation Co., Ltd., Seoul (KR); SK Global Chemical Co., Ltd., Seoul (KR)

(72) Inventors: Ho Seong Lee, Daejeon (KR); Jin Haek Yang, Daejeon (KR); Myoung Lae Kim, Daejeon (KR); Yong Nam Joe, Daejeon (KR)

(73) Assignees: SK Innovation Co., Ltd., Seoul (KR); SK Global Chemical Co., Ltd., Seoul (KR)

( * ) Notice: Subject to any disclaimer, the term of this patent is extended or adjusted under 35 U.S.C. 154(b) by 54 days.

(21) Appl. No.: 16/622,055

(22) PCT Filed: May 15, 2018

(86) PCT No.: PCT/KR2018/005523
§ 371 (c)(1),
(2) Date: Dec. 12, 2019

(87) PCT Pub. No.: WO2018/230846
PCT Pub. Date: Dec. 20, 2018

(30) Foreign Application Priority Data

Jun. 16, 2017 (KR) .................... 10-2017-0076510

(51) Int. Cl.
*B01J 31/12* (2006.01)
*C07C 2/30* (2006.01)
*B01J 31/14* (2006.01)
*C07C 11/107* (2006.01)
*C07C 11/04* (2006.01)

(52) U.S. Cl.
CPC ............... *B01J 31/143* (2013.01); *C07C 2/30* (2013.01); *C07C 11/04* (2013.01); *C07C 11/107* (2013.01)

(58) Field of Classification Search
None
See application file for complete search history.

(56) References Cited

U.S. PATENT DOCUMENTS

| 6,723,806 B2 | 4/2004 | Van Tol et al. |
| 6,800,702 B2 | 10/2004 | Wass |
| 7,511,183 B2 | 3/2009 | Blann et al. |
| 2013/0131284 A1 | 5/2013 | Azap et al. |
| 2013/0158282 A1 | 6/2013 | Christiansen et al. |
| 2014/0094620 A1 | 4/2014 | Yang et al. |

FOREIGN PATENT DOCUMENTS

| JP | 20020519358 A | 7/2002 |
| JP | 4228092 B2 | 2/2009 |
| JP | 5864447 B2 | 2/2016 |
| KR | 1020130010074 A | 1/2013 |
| KR | 1020150108158 A | 9/2015 |
| WO | 0204119 A1 | 1/2002 |
| WO | 2004056479 A1 | 7/2004 |

OTHER PUBLICATIONS

Feher et al., "Cross-metathesis of alkenes with vinyl-substituted silsesquioxanes and spherpsilicates: a new method for synthesizing highly-functionalized Si/O frameworks", Chemical Communications, Issue 13, 1997, pp. 1185-1186. (Year: 1997).*
Fei et al., "Silsesquioxane Chemistry, 12[1] Preparation and Complexation of a Novel Silsesquioxanyl Phosphine Ligand", Journal of Inorganic and General Chemistry, 2003, vol. 623, Issue 2, 2003, pp. 353-356. (Year: 2003).*
Ropartz et al., "Hydrocarbonylation reactions using alkylphosphine-containing dendrimers based on a polyhedral oligosilsesquioxane core", Journal of the Chemical Society, Dalton Transactions, 2002, pp. 1997-2008. (Year: 2002).*
Carter et al., "High activity ethylene trimerisation catalysts based on diphosphine ligands", Chemical Communications, 2002, pp. 858-859, vol. 8.
Lee et al., "Polyhedral oligomeric silsesquioxane-conjugated bis(diphenylphosphino) amine ligand for chromium (III) catalyzed ethylene trimerization and tetramerization", Applied Catalysis A, General, 2018, pp. 21-27, vol. 560.
Qi et al., "High-efficiency flame retardancy of epoxy resin composites with perfect T8 caged phosphorus containing polyhedral oligomeric silsesquioxanes (P-POSSs)", Composites Science and Technology, 2016, pp. 8-19, vol. 127.
Ropartz et al., "Phosphine-containing carbosilane dendrimers based on polyhedral silsesquioxane cores as ligands for hydroformylation reaction of oct-1-ene", Journal of Molecular Catalysis A: Chemical, 2002, pp. 99-105, vols. 182-183.

* cited by examiner

Primary Examiner — Philip Y Louie
(74) Attorney, Agent, or Firm — The Webb Law Firm

(57) ABSTRACT

The present invention relates to a heteroatom ligand, an oligomerization catalyst containing the same, and a method for preparing an oligomer by using the same. Specifically, the present invention relates to a heteroatom ligand having a silsesquioxane derivative, an oligomerization catalyst containing the same, and a method for preparing an oligomer by using the same.

15 Claims, No Drawings

HETEROATOM LIGAND, OLIGOMERIZATION CATALYST CONTAINING SAME, AND METHOD FOR PREPARING OLIGOMER

CROSS-REFERENCE TO RELATED APPLICATIONS

This application is the United States national phase of International Application No. PCT/KR2018/005523 filed May 15, 2018, and claims priority to Korean Patent Application No. 10-2017/0076510 filed Jun. 16, 2017, the disclosures of which are hereby incorporated by reference in their entirety.

TECHNICAL FIELD

The present invention relates to a heteroatom ligand, an oligomerization catalyst including the same, and a method for preparing an oligomer using the oligomerization catalyst.

BACKGROUND ART

An oligomer, specifically 1-hexene or 1-octene is an important commercial raw material which is widely used in a polymerization process as a monomer or comonomer for preparing a linear low-density polyethylene, and is obtained by purifying a product produced by an oligomerization reaction of ethylene. However, a conventional ethylene oligomerization reaction had an inefficient aspect of producing significant amounts of butene, higher oligomers, and polyethylene together with 1-hexene and 1-octene. Since the conventional ethylene oligomerization technique as such generally produces various α-olefins depending on a Schulze-Flory or Poisson product distribution, a product yield to be desired is limited.

Recently, a study on selectively trimerizing ethylene to produce 1-hexene or selectively tetramerizing ethylene to produce 1-octeneis by transition metal catalysis has been conducted, and most of the known transition metal catalysts are chromium-based catalysts.

International Patent Publication No. WO 02/04119 discloses a chromium-based catalyst using a ligand represented by a general formula of $(R^1)(R^2)X—Y—X(R^3)(R^4)$ as an ethylene trimerization catalyst, wherein X is phosphorus, arsenic, or antimony, Y is a linking group such as $—N(R^5)—$, and at least one of $R^1, R^2, R^3$, and $R^4$ has a polar or electron donating substituent.

Another known document discloses a use of (o-ethylphenyl)$_2$PN(Me)P(o-ethylphenyl)$_2$ which is a compound having no polar substituent on at least one of $R^1, R^2, R^3$, and $R^4$ as a ligand representing a catalyst activity on 1-hexene under a catalyst condition (Antea Carter et al., Chem. Commun., 2002, p. 858-859).

Meanwhile, it is known from International Patent Publication No. WO 04/056479 that ethylene is tetramerized by a chromium-based catalyst including a PNP ligand from which a substituent is omitted on a phenyl ring attached to phosphorus, thereby improving selectivity in producing 1-octene, and the document discloses (phenyl)$_2$PN(isopropyl)P(phenyl)$_2$ and the like as an example of a heteroatom ligand used for a tetramerization catalyst for tetramerization of these ethylenes.

The related art document discloses that the chromium-based catalyst including a heteroatom ligand having nitrogen and phosphorus as a heteroatom tetramerizes ethylene without a polar substituent for a hydrocarbyl or heterohydrocarbyl group bonded to a phosphorus atom, thereby producing 1-octene in a selectivity of more than 70% by mass.

However, the related art documents do not suggest a clear example as to specifically what form may tetramerize ethylene highly selectively to produce 1-octene or trimerize ethylene to produce 1-hexene, regarding a structure of a ligand containing a heteroatom, suggests only a structure of a PNP type skeleton such as $(R^1)(R^2)P—(R^5)N—P(R^3)(R^4)$ as a ligand having a 1-octene selectivity of about 70% by mass, and only limitedly suggests a substitutable substituent form from among the heteroatom ligands.

Meanwhile, in a catalyst system for tetramerization of ethylene, a catalyst activity at a high reaction temperature is decreased, a considerable polymer byproduct is formed to lower the selectivity, and serious problems are caused in a polymerization process.

Specifically, a tetramerization has decreased catalyst activity at a high temperature to decrease the productivity and selectivity of olefins, in particular 1-octene, and increase production of byproducts. This causes tube blockage and fouling, leading to shut down inevitably, thereby causing serious problems in an olefin polymerization process.

Accordingly, it is required to develop an olefin oligomerization catalyst having a structure in which olefin oligomerization catalyst activity is not decreased even at a high temperature while it is easy to adjust a catalyst amount, and olefin is oligomerized with high activity and high selectivity to produce 1-hexene or 1-octene.

DISCLOSURE

Technical Problem

An object of the present invention is to provide a heteroatom ligand having excellent catalyst activity at the time of olefin oligomerization simultaneously with high solubility in a solvent to easily adjust a catalyst amount and maintain activity even at a high temperature, thereby being capable of producing an oligomer with high activity and high selectivity.

Another object of the present invention is to provide an oligomerization catalyst including a transition metal coordinated with a heteroatom ligand and an organic ligand and a cocatalyst and a method for preparing an oligomer using the same.

Technical Solution

In one general aspect, a heteroatom ligand oligomerizes an olefin with high activity and high selectivity even at a high temperature for use in oligomerization of an olefin, specifically trimerization or tetramerization of ethylene, and is represented by the following Chemical Formula 1:

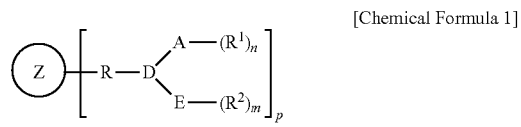

[Chemical Formula 1]

wherein

A and E are independently of each other selected from the group consisting of phosphorus, arsenic, antimony, oxygen, bismuth, sulfur, selenium, and nitrogen, D is a linking group between A and E, Z is a silsesquioxane derivative, R is hydrocarbylene, $R_1$ and $R_2$ are independently of each other substituted or unsubstituted hydrocarbyl or substituted or unsubstituted heterohydrocarbyl, p is an integer of 1 to 18, and varies with the number of Si contained in the silsesquioxane derivative, and n and m are independently of each other determined by each valency or oxidation state of A or E.

In Chemical Formula 1 according to an exemplary embodiment of the present invention, the silsesquioxane derivative may be represented by the following Chemical Formula 2:

$$*-(SiO_{3/2})_q(R^7)_{q-1} \qquad \text{[Chemical Formula 2]}$$

wherein $R^7$ is hydrogen, hydroxy, halogen, hydrocarbyl, substituted hydrocarbyl, heterohydrocarbyl, or substituted heterohydrocarbyl, and q is 2, 4, 6, 8, 10, 12, 14, 16, or 18.

In addition, $R^7$ is C6-C20aryl, C1-C10alkyl, C2-C10alkenyl, C2-C10alkynyl, C1-C10alkoxy, C6-C20arylC1-C10alkyl, C1-C10alkylC6-C20aryl, C3-C10cycloalkyl, C3-C10heterocycloalkyl, or C3-C20heteroaryl, wherein $R^7$ may be substituted by any one or more selected from the group consisting of halogens, nitro, amino, cyano, C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C10cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, and C2-C10heterocycloalkyl. In addition, q may be an integer of 8.

Specifically, $R^7$ may be C1-C10alkyl.

In Chemical Formula 1, D may be any one selected from the group consisting of organic linking groups including substituted or unsubstituted hydrocarbylene or substituted or unsubstituted heterohydrocarbylene; and inorganic linking groups including a single atomic link.

In terms of having excellent catalyst activity and solubility even at a high temperature, preferably, Chemical Formula 1 may be selected from the following Chemical Formulae 3 to 5:

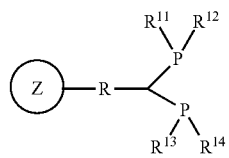

[Chemical Formula 3]

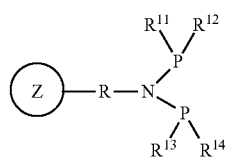

[Chemical Formula 4]

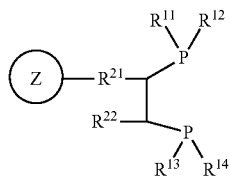

[Chemical Formula 5]

wherein

Z is a silsesquioxane derivative, $R^{11}$ to $R^{14}$ are independently of one another hydrocarbyl, substituted hydrocarbyl, heterohydrocarbyl, or substituted hydrocarbyl, specifically independently of one another C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C10cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, 5- to 7-membered heterocycloalkyl or —$NR^{31}R^{32}$, wherein $R^{31}$ and $R^{32}$ are independently of each other C1-C10alkyl, C2-C10alkenyl, C2-C10alkynyl, C6-C20aryl, diC1-C10alkylamino, diC2-C10alkenylamino, or diC2-C10alkynylamino, R and $R^{21}$ are independently of each other C6-C20arylene, C6-C20aryleneC1-C10alkylene, C6-C20aryleneC2-C10alkenylene, C6-C20aryleneC2-C10alkynylene, C1-C10alkylene, C2-C10alkenylene, C2-C10alkynylene, or C3-C20heteroarylene, $R^{22}$ is C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C3-C20heteroaryl, or

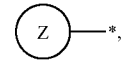

and arylene, arylenealkylene, arylenealkenylene, arylenealkynylene, alkylene, alkenylene, alkynylene, and heteroarylene of R, $R^{21}$, aryl, arylalkyl, arylalkenyl, arylalkynyl, alkyl, alkenyl, alkynyl, and heteroaryl of $R^{22}$ and aryl, arylalkyl, alkyl, arylalkenyl, alkenyl, arylalkynyl, alkynyl, alkoxy, aryloxy, cycloalkyl, heteroaryl, and heterocycloalkyl of $R^{11}$ to $R^{14}$ may be further substituted by one or more selected from the group consisting of halogens, C1-C10alkyl, haloC1-C10alkyl, C2-C10alkenyl, C2-C10alkynyl, C1-C10alkoxy, haloC1-C10alkoxy, C6-C20aryl, and C6-C20aryloxy.

Preferably, they may be further substituted by one or more selected from the group consisting of halogen, C1-C10alkyl, haloC1-C10alkyl, C2-C10alkenyl, C2-C10alkynyl, C1-C10alkoxy, and haloC1-C10alkoxy.

More preferably, in Chemical Formulae 3 to 5, $R^{11}$ to $R^{14}$ are independently of one another C6-C20aryl, C6-C20arylC1-C10alkyl, C6-C20arylC2-C10alkenyl, or C6-C20arylC2-C10alkynyl; R and $R^{21}$ are independently of each other C1-C10alkylene, $R^{22}$ is C1-C10alkyl or

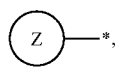

aryl, arylalkyl, arylalkenyl, and arylalkynyl of $R^{11}$ to $R^{14}$, alkylene of $R^{21}$ and alkyl of $R^{22}$ may be further substituted by one or more selected from the group consisting of halogens, C1-C10alkyl, haloC1-C10alkyl, C1-C10alkoxy, haloC1-C10alkoxy, C6-C20aryl, and C6-C20aryloxy.

Preferably, the silsesquioxane derivative in Chemical Formulae 3 to 5 may be *—$(SiO_{3/2})_q(R^7)_{q-1}$ (wherein $R^7$ and q are as defined in Chemical Formula 2).

In another general aspect, an oligomerization catalyst includes the heteroatom ligand of the present invention and a transition metal.

In still another general aspect, a method for preparing an oligomer includes introducing an oligomerization catalyst to a reactor, introducing an olefin to the reactor, and reacting the olefin with the oligomerization catalyst to perform oligomerization.

A cocatalyst according to an exemplary embodiment of the present invention may be an organic aluminum compound, organic aluminoxane, an organic boron compound, an organic salt, or a mixture thereof, and specifically, one or a mixture or two or more selected from the group consisting of methylaluminoxane (MAO), modified methylaluminoxane (MAO), ethylaluminoxane (EAO), tetraisobutylaluminoxane (TIBAO), isobutylaluminoxane (IBAO), trimethylaluminum (TMA), triethylaluminum (TEA), triisobutylaluminum (TIBA), tri-n-octylaluminum, methylaluminumdichloride, ethylaluminum dichloride, dimethylaluminum chloride, diethylaluminum chloride, aluminumisopropoxide, ethylaluminum sesquichloride, and methylaluminum sesquichloride.

The method for preparing an oligomer according to an exemplary embodiment of the present invention may further include introducing a cocatalyst containing a metal in an amount of 100 to 5,000 times the moles of the transition metal to the reactor.

In the method for preparing an oligomer according to an exemplary embodiment of the present invention, the olefin may be ethylene, and the oligomer may be 1-hexene, 1-octene, or a mixture thereof.

Advantageous Effects

The heteroatom ligand having a silsesquioxane derivative of the present invention is coordinated with a transition metal, whereby catalyst activity and selectivity are excellent even at a high temperature, and furthermore, solubility in a solvent is high, so that an aliphatic hydrocarbon compound may be used as a reaction solvent instead of a conventionally used aromatic hydrocarbon compound, an oligomer may be prepared with high activity even with a small amount of catalyst, and an introduction amount of a catalyst may be easily adjusted.

In addition, the oligomerization catalyst of the present invention has excellent catalyst activity even at a high temperature, has a high solubility in a solvent to maintain catalyst activity, allows mass production with a use of a small amount of the cocatalyst, and does not cause fouling and tube blockage which occurs in a high temperature process so that shut down is not required, and thus, is very economical.

In addition, the method for preparing an oligomer of the present invention may produce an oligomer with high activity and high selectivity even at a high temperature, and does not cause fouling and tube blockage, and thus, allows preparation of an olefin with a very efficient process.

BEST MODE

"Hydrocarbyl" or "heterohydrocarbyl" described herein refers to a radical having one binding site derived from hydrocarbon or heterohydrocarbon, "hydrocarbylene" refers to a radical having two binding sites derived from hydrocarbon, and "hetero" refers to a carbon being substituted by one or more atoms selected from the group consisting of O, S and N atoms.

"Substituted" described herein refers to a group or a site having one or more substituents attached to a structural skeleton of a group or part. It means that the mentioned group or structural skeleton is substituted by any one or more selected from the group consisting of deuterium, hydroxy, halogen, carboxyl, cyano, nitro, oxo (=O), thio (=S), alkyl, haloalkoxy, alkenyl, alkynyl, aryl, aryloxy, alkoxycarbonyl, alkylcarbonyloxy, alkenylcarbonyloxy, alkynylcarbonyloxy, aminocarbonyl, alkylcarbonylamino, alkenylcarbonylamino, alkylcarbonylamino, alkenylcarbonylamino, alkynylcarbonylamino, thioalkyl, thioalkenyl, thioalkynyl, alkylsilyl, alkenylsilyl, alkynylsilyl, arylsilyl, arylalkyl, arylalkenyl, arylalkynyl, cycloalkyl, cycloalkylalkyl, cycloalkenyl, amino, alkylamino, dialkylamino, heteroaryl, a heterocyclylalkyl ring, heteroarylalkyl, and heterocycloalkyl.

Specifically, it means that the mentioned group or structural skeleton is substituted by any one or more selected from the group consisting of deuterium, hydroxy, halogen, carboxyl, cyano, nitro, oxo(=O), thio(=S), C1-C10alkyl, haloC1-C10 alkoxy, C2-C10alkenyl, C2-C10alkynyl, C6-C20aryl, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkylcarbonylamino, C2-C10alkenylcarbonylamino, C2-C10alkynylcarbonylamino, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C6-C20arylC1-C10alkyl, C6-C20arylC2-C10alkenyl, C6-C20arylC2-C10alkynyl, C3-C10cycloalkyl, C3-C10cycloalkylC1-C10alkyl, C2-C10cycloalkenyl, amino, C1-C10alkylamino, diC1-C10alkylamino, C6-C20heteroaryl, C3-C20heterocycloalkyl ring, C3-C10heteroarylC1-C10alkyl, and C3-C10heterocycloalkyl.

"Alkene" described herein refers to a straight chain, branched chain, or cyclic hydrocarbon containing one or more carbon-to-carbon double bonds.

"Alkyne" described herein refers to a straight chain, branched chain, or cyclic hydrocarbon containing one or more carbon-to-carbon triple bonds, and the alkene and alkyne described in the present invention may have, as an example, 2 to 10 carbon atoms, preferably 2 to 7 carbon atoms.

"Alkyl", "alkoxy", and other substituents containing an "alkyl" moiety described herein include both straight chain or branched chain forms, and have, as an example, 1 to 10 carbon atoms, preferably 1 to 7 carbon atoms, more preferably 1 to 5 carbon atoms.

In addition, "aryl" described herein refers to an organic radical derived from an aromatic hydrocarbon by removal of one hydrogen, including a single- or fused ring system containing, as an example, 4 to 7, preferably 5 or 6 ring atoms in each ring, and even a form in which a plurality of aryls are linked by a single bond. Specific examples thereof include phenyl, naphthyl, biphenyl, anthryl, indenyl, fluorenyl, and the like, but are not limited thereto.

"Heteroaryl" described herein refers to an aryl group containing one or more atoms selected from the group consisting of B, N, O, S, P(=O), Si, and P as an aromatic ring skeleton atom and carbon as a remaining aromatic ring skeleton atom. As an example, "heteroaryl" is a 5- to 6-membered monocyclic heteroaryl, or a polycyclic heteroaryl condensed with one or more benzene rings, and may be partially saturated. In addition, the heteroaryl in the present invention also includes a form in which one or more heteroaryls are linked by a single bond.

The term "alkenyl" described herein alone or as a part of another group refers to a straight chain, branched chain, or cyclic hydrocarbon radical containing one or more carbon-to-carbon double bonds. As an example, the alkenyl radical is a lower alkenyl radical having 2 to 10, preferably 2 to about 7 carbon atoms. The most preferred lower alkenyl radical is a radical having 2 to about 5 carbon atoms. In addition, the alkenyl group may be substituted at any usable attachment point. An example of the alkenyl radical includes ethenyl, propenyl, allyl, butenyl and 4-methylbutenyl. The terms alkenyl and lower alkenyl include radicals being cis- and trans-oriented, or alternatively, having E and Z orientations The term "alkynyl" described herein alone or as a part of another group refers to a straight chain, branched chain, or cyclic hydrocarbon radical containing one or more carbon-to-carbon triple bonds. The alkenyl radical is a lower alkynyl radical having, as an example, 2 to 10, preferably 2 to about 7 carbon atoms. The most preferred is a lower alkenyl radical having 2 to about 5 carbon atoms. Examples of the radical include propargyl, butynyl, and the like. In addition, the alkynyl group may be substituted at any usable attachment point.

"Cycloalkyl" described herein refers to a non-aromatic monocyclic or polycyclic system, having preferably 3 to 10 carbon atoms. The monocyclic ring includes cyclopropyl, cyclobutyl, cyclopentyl, and cyclohexyl, without limitation. An example of the polycyclic cycloalkyl group includes perhydronaphthyl, perhydroindenyl, and the like; and a bridged polycyclic cycloalkyl group includes adamantyl, norbornyl, and the like.

"Heterocycloalkyl" described herein refers to a substituted or unsubstituted non-aromatic 3- to 15-membered ring radical consisting of carbon atoms and 1 to 5 heteroatoms selected from the group consisting of nitrogen, phosphorus, oxygen, and sulfur; a heterocycloalkyl radical may be a monocyclic, bicyclic, or tricyclic ring system which may be fused or bridged or include a spirocyclic system; and if necessary, a nitrogen, phosphorus, carbon, oxygen, or sulfur atom in the heterocyclic ring radical may be oxidized to various oxidation states in some cases. In addition, if necessary, a nitrogen atom may be quaternarized.

"An alicyclic ring" described herein refers to a non-aromatic monocyclic or polycyclic ring system, and the carbon in the ring may have a carbon-carbon double bond or a carbon-carbon triple bond. The alicyclic ring may have preferably 3 to 10 carbon atoms.

"An oligomerization catalyst" herein is defined as including both a transition metal complex form prepared with a ligand and a transition metal and a composition form of a ligand and a transition metal.

"An oligomerization catalyst composition" herein is defined as further including a cocatalyst or an additive in the "oligomerization catalyst" described above.

The present invention provides an oligomerization catalyst having a surprisingly improved solubility in a solvent while maintaining high activity at a high temperature, unlike a conventional catalyst, and the oligomerization catalyst according to an exemplary embodiment of the present invention includes a heteroatom ligand represented by the following Chemical Formula 1:

[Chemical Formula 1]

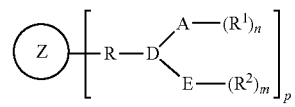

wherein

A and E are independently of each other selected from the group consisting of phosphorus, arsenic, antimony, oxygen, bismuth, sulfur, selenium, and nitrogen, D is a linking group between A and E, Z a silsesquioxane derivative, R is hydrocarbylene, $R_1$ and $R_2$ are independently of each other substituted or unsubstituted hydrocarbyl or substituted or unsubstituted heterohydrocarbyl, p is an integer of 1 to 18, and n and m are independently of each other determined by each valency or oxidation state of A or E.

In Chemical Formula 1, p varies with the silsesquioxane derivative, specifically the number of Si possessed by the silsesquioxane derivative, and as an example, in Chemical Formula 1, when silsesquioxane is POSS, p may be an integer of 1 to 8.

In terms of having high activity and high selectivity, in Chemical Formula 1, the silsesquioxane derivative may be represented by the following Chemical Formula 2:

$$*-(SiO_{3/2})_q(R^7)_{q-1} \qquad \text{[Chemical Formula 2]}$$

wherein $R^7$ is hydrocarbyl, substituted hydrocarbyl, heterohydrocarbyl, or substituted heterohydrocarbyl, and q is an integer of 2, 4, 6, 8, 10, 12, 14, 16, or 18.

Preferably, in Chemical. Formula 2 according to an exemplary embodiment of the present invention, $R^7$ is hydrogen, hydroxy, a halogen, C6-C20aryl, C1-C10alkyl, C2-C10alkenyl, C2-C10alkynyl, C1-C10alkoxy, C6-C20arylC1-C10alkyl, C1-C10alkylC6-C20aryl, C3-C10cycloalkyl, C3-C10heterocycloalkyl, or C3-C20heteroaryl, and the aryl, alkyl, alkenyl, alkynyl, alkoxy, arylalkyl, alkylaryl, cycloalkyl, heterocycloalkyl, and heteroaryl may be further substituted by any one or more selected from the group consisting of halogens, nitro, amino, cyano, C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C10cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, and C2-C10heterocycloalkyl; and preferably, $R^7$ is hydrogen, C6-C20aryl, C1-C10alkyl, C1-C10alkoxy, C3-C10cycloalkyl, C3-C10heterocycloalkyl, or C3-C20heteroaryl, and the aryl, alkyl, alkoxy, cycloalkyl, heterocycloalkyl, and heteroaryl may be further substituted by any one or more selected from the group consisting of halogen, nitro, amino, cyano, C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C10cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, and C2-C10heterocycloalkyl.

In Chemical Formula 2, q may be preferably an integer of 4, 6, 8, or 10, and more preferably an integer of 8.

More preferably, in Chemical Formula 2, $R^7$ may be hydrogen, C6-C20aryl, C1-C10alkyl, or C3-C10cycloalkyl, more preferably C1-C10alkyl, and q may be an integer of 8.

In Chemical Formula 1, D may be any one selected from the group consisting of organic linking groups including substituted or unsubstituted hydrocarbylene or substituted or unsubstituted heterohydrocarbylene; and inorganic linking groups including a single atom link, and in Chemical Formula 1 according to an exemplary embodiment of the present invention, R may be C6-C20arylene or C1-C10alkylene, preferably C1-C10alkylene.

Preferably, the heteroatom ligand according to an exemplary embodiment of the present invention may be selected from the following Chemical Formula 3 to 5:

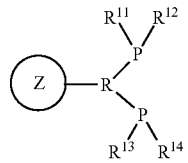

[Chemical Formula 3]

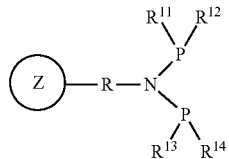

[Chemical Formula 4]

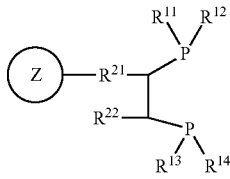

[Chemical Formula 5]

wherein

Z is a silsesquioxane derivative, $R^{11}$ to $R^{14}$ are independently of one another C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C10cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, 5- to 7-membered heterocycloalkyl or $-NR^{31}R^{32}$, wherein Rn and $R^{32}$ are independently of each other C1-C10alkyl, C2-C10alkenyl, C2-C10alkynyl, C6-C20aryl, diC1-C10alkylamino, diC2-C10alkenylamino, or diC2-C10alkynylamino, R and $R^{21}$ are independently of each other C6-C20arylene, C6-C20aryleneC1-C10alkylene, C6-C20aryleneC2-C10alkenylene, C6-C20aryleneC2-C10alkynylene, C1-C10alkylene, C2-C10alkenylene, C2-C10alkynylene, or C3-C20heteroarylene, $R^{22}$ is C6-C20aryl, C6-C20aryleneC1-C10alkyl, C6-20arylC2-C10alkenyl, C6-C20arylC2-C10alkynyl, C1-10alkyl, C2-C10alkenyl, C2-C10-alkynyl, C3-C20heteroaryl, or

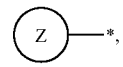

and arylene, arylenealkylene, arylenealkenylene, arylenealkynylene, alkylene, alkenylene, alkynylene, and heteroarylene of R, $R^{21}$, aryl, arylalkyl, arylalkenyl, arylalkynyl, alkyl, alkenyl, alkynyl, and heteroaryl of $R^{22}$ and aryl, arylalkyl, alkyl, arylalkenyl, alkenyl, arylalkynyl, alkynyl, alkoxy, aryloxy, cycloalkyl, heteroaryl, and heterocycloalkyl of $R^{11}$ to $R^{14}$ may be further substituted by one or more selected from the group consisting of halogen, C1-C10alkyl, haloC1-C10alkyl, C2-C10alkenyl, C2-C10alkynyl, C1-C10alkoxy, haloC1-C10alkoxy, C6-C20aryl, and C6-C20aryloxy.

Preferably, in Chemical Formulae 3 to 5, $R^{11}$ to $R^{14}$ are independently of one another C6-C20aryl, C6-C20arylC1-C10alkyl, C6-C20arylC2-C10alkenyl, or C6-C20arylC2-C10alkynyl, R and $R^{21}$ are independently of each other C1-C10alkylene, $R^{22}$ is C1-C10alkyl or

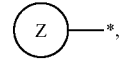

and the aryl, arylalkyl, arylalkenyl, and arylalkynyl of $R^{11}$ to $R^{14}$, the alkylene of $R^{21}$ and alkyl of $R^{22}$ may be further substituted by one or more selected from the group consisting of halogen, C1-C10alkyl, haloC1-C10alkyl, C1-C10alkoxy, haloC1-C10alkoxy, C6-C20aryl, and C6-C20aryloxy.

Preferably, the silsesquioxane derivative in Chemical Formulae 3 to 5 is $*-(SiO_{3/2})_q(R^7)_{q-1}$, wherein $R^7$ is hydrocarbyl, substituted hydrocarbyl, heterohydrocarbyl, or substituted heterohydrocarbyl, preferably C1-C10alkyl, and q may be an integer of 2, 4, 6, 8, 10, 12, 14, 16, or 18, and preferably an integer of 8.

Specifically, the oligomerization catalyst according to an exemplary embodiment of the present invention includes a heteroatom ligand and a transition metal, and the oligomerization catalyst composition according to an exemplary embodiment of the present invention may include the oligomerization catalyst and a cocatalyst.

The oligomerization catalyst according to an exemplary embodiment of the present invention may be prepared by including the heteroatom ligand, and may be prepared by further including an organic ligand and a transition metal compound.

The oligomerization catalyst prepared with a transition metal compound including the heteroatom ligand according to an exemplary embodiment of the present invention and an organic ligand may be represented by the following Chemical Formula 6:

[Chemical Formula 6]

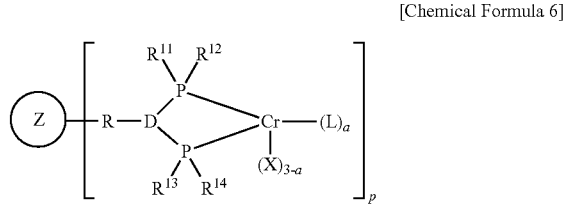

wherein

Z is a silsesquioxane derivative,

D is selected from the group consisting of organic linking groups including substituted or unsubstituted hydrocarbylene or substituted or unsubstituted heterohydrocarbylene; and inorganic linking groups including a single atom link, R is hydrocarbylene, $R^{11}$ to $R^{14}$ are independently of one another hydrocarbyl, L is an organic ligand, X is a halogen, a is 0 or an integer of 1 to 3, and when a is an integer of 2 or more, L may be identical to or different from each other, and p is an integer of 1 to 8.

Preferably, in Chemical Formula 6 according to an exemplary embodiment of the present invention, p may be an integer of 1 to 4, more preferably 1.

Preferably, the oligomerization catalyst including the heteroatom ligand including the silsesquioxane represented by Chemical Formula 6 may be represented by the following Chemical Formulae 7 to 9:

[Chemical Formula 7]

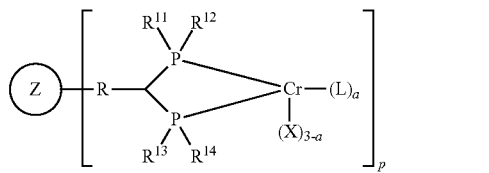

[Chemical Formula 8]

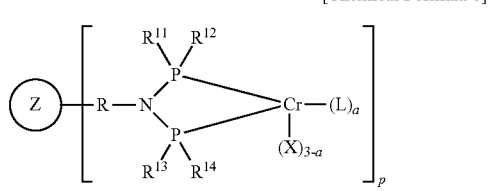

[Chemical Formula 9]

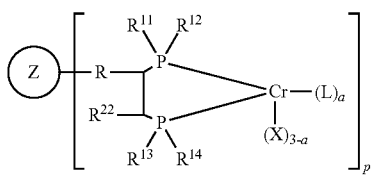

wherein

Z is a silsesquioxane derivative,

R and $R^{21}$ are independently of each other C6-C20arylene, C6-C20aryleneC1-C10alkylene, C6-C20aryleneC2-C10alkenylene, C6-C20aryleneC2-C10alkynylene, C1-C10alkylene, C2-C10alkenylene, C2-C10alkynylene, or C3-C20heteroarylene, $R^{22}$ is C1-C10alkyl or

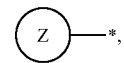

and $R^{11}$ to $R^{14}$ are independently of one another C6-C20aryl, C6-C20arylC1-C10alkyl, C6-C20arylC2-C10alkenyl, C6-C20arylC2-C10alkynyl, C1-C10alkyl, C2-C10alkenyl, C2-C10alkynyl, C1-C10alkoxy, C6-C20aryloxy, C1-C10alkoxycarbonyl, C1-C10alkylcarbonyloxy, C2-C10alkenylcarbonyloxy, C2-C10alkynylcarbonyloxy, aminocarbonyl, C1-C10alkylcarbonylamino, C2-C10alkenylcarbonylamino, C2-C10alkynylcarbonylamino, C3-C7cycloalkyl, thioC1-C10alkyl, thioC2-C10alkenyl, thioC2-C10alkynyl, C1-C10alkylsilyl, C2-C10alkenylsilyl, C2-C10alkynylsilyl, C6-C20arylsilyl, C3-C20heteroaryl, 5- to 7-membered heterocycloalkyl or —NR$^{31}$R$^{32}$, wherein R$^{31}$ and R$^{32}$ are independently of each other C1-C10alkyl, C2-C10alkenyl, C2-C10alkynyl, C6-C20aryl, diC1-C10alkylamino, diC2-C10alkenylamino, or diC2-C10alkynylamino, L is an organic ligand, X is a halogen, a is 0 or an integer of 1 to 3, and when a is an integer of 2 or more, L may be identical to or different from each other, and p is an integer of 1 to 8, and arylene, arylenealkylene, arylenealkenylene, arylenealkynylene, alkylene, alkenylene, alkynylene, and heteroarylene of R and $R^{21}$, alkylene of $R^{22}$ and aryl, arylalkyl, alkyl, arylalkenyl, alkenyl, arylalkynyl, alkynyl, alkoxy, aryloxy, cycloalkyl, heteroaryl, and heterocycloalkyl of $R^{11}$ to $R^{14}$ may be further substituted by one or more selected from the group consisting of C1-C10alkyl, haloC1-C10alkyl, C2-C10alkenyl, C2-C10alkynyl, C1-C10alkoxy, haloC1-C10alkoxy, C6-C20aryl, C6-C20aryloxy, and halogen.

The transition metal compound according to an exemplary embodiment of the present invention may further include an organic ligand.

The transition metal compound including an organic ligand may be represented by the following Chemical Formula 10, but is not limited thereto:

$$M(L^1)_s(L^2)_t$$ [Chemical Formula 10]

wherein M is a transition metal, $L^1$ and $L^2$ are an organic ligand, and s and t are independently of each other an integer of 0 or more and have an oxidation number of s+t=M.

In Chemical Formula 10, the transition metal is not particularly limited, but may be Group 4, Group 5, or Group 6 transition metals, preferably, may be selected from the group consisting of chromium, molybdenum, tungsten, titanium, tantalum, vanadium, or zirconium, and more preferably, may be chrome.

In Chemical Formula 10, any organic ligand is possible as long as it may be bonded to a transition metal, and as an example, the organic ligand may be selected from the group consisting of halogen, alkyl, alkene, alkenyl, cycloalkyl, heterocycloalkyl, aryl, and heteroaryl.

Specifically, L in Chemical Formulae 6 to 9 and $L^1$ and $L^2$ in Chemical Formula 10, which are the organic ligand according to an exemplary embodiment of the present invention, may be independently of each other selected from the group consisting of halogen, C1-C10alkyl, C3-C10cycloalkyl, C3-C10heterocycloalkyl, or the following structural formula, but is not limited thereto.

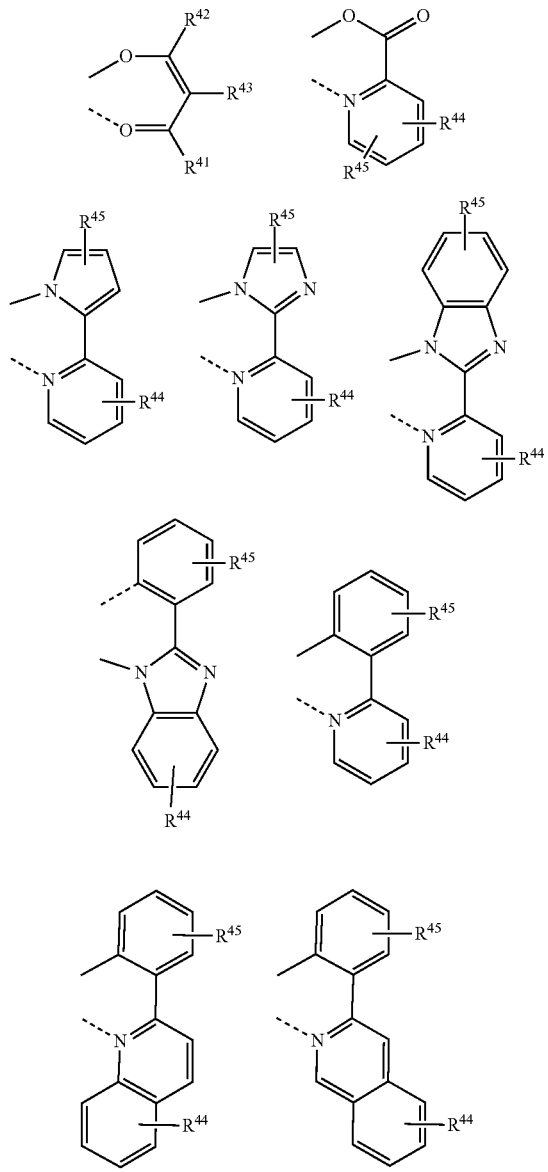

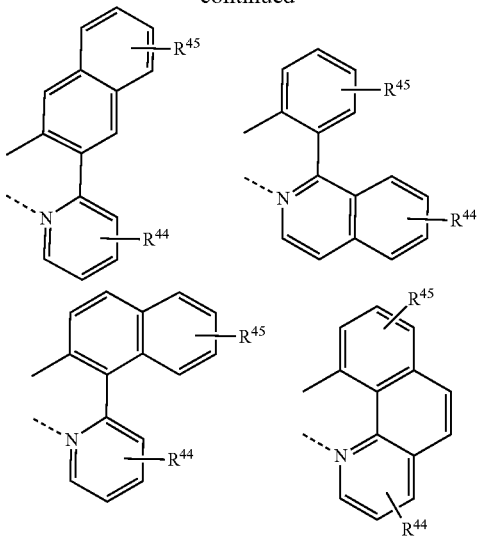

In the above structural formula, $R^{41}$ and $R^{42}$ are independently of each other hydrocarbyl, substituted hydrocarbyl, heterohydrocarbyl, or substituted hydrocarbyl, $R^{43}$ is hydrogen, halogen, hydrocarbyl, substituted hydrocarbyl, heterohydrocarbyl, or substituted heterohydrocarbyl;

$R^{44}$ and $R^{45}$ are independently of each other hydrogen, hydrocarbyl, substituted hydrocarbyl, heterohydrocarbyl, or substituted heterohydrocarbyl.

L in Chemical Formulae 6 to 9 and $L^1$ and $L^2$ in Chemical Formula 10 may be preferably C3-C10heterocycloalkyl. The oligomerization catalyst according to an exemplary embodiment of the present invention includes a heteroatom ligand, whereby solubility is excellent to have excellent catalyst activity without using a large amount of a cocatalyst, an introduction amount of the catalyst at the time of oligomerization of an olefin may be adjusted, and furthermore, excellent activity is maintained even at a high temperature, so that tube blockage and fouling do not occur in an olefin preparation process, and thus, the oligomerization catalyst is very economical and efficient.

Specifically, the oligomerization catalyst according to an exemplary embodiment of the present invention has a heteroatom ligand having a silsesquioxane derivative, whereby selectivity at the time of olefin polymerization using the catalyst is very high, activity at a high temperature is excellent, solubility of the oligomerization catalyst is excellent, so that various solvents may be used, and thus, the oligomerization catalyst is applicable to various process conditions and allows mass production.

The cocatalyst may be an organic aluminum compound, an organic aluminoxane, an organic boron compound, an organic salt, or a mixture thereof.

The organic aluminum compound may include a compound of $Al(R^a)_3$ (wherein $R^a$ is independently of each other C1-C12alkyl, C2-C10alkenyl, C2-C10alkynyl, C1-C12alkoxy, or a halogen) or $LiAlH_4$ and the like.

The organic aluminum compound may include one or a mixture or two or more selected from the group consisting of trimethylaluminum (TMA), triethylaluminum (TEA), triisobutylaluminum (TIBA), tri-n-octylaluminum, methylaluminum dichloride, ethylaluminum dichloride, dimethylaluminum chloride, diethylaluminum chloride, aluminum isopropoxide, ethylaluminum sesquichloride, and methylaluminum sesquichloride.

The organic aluminoxane may be an oligomer compound which may be prepared by adding water and an alkylaluminum compound, for example, by adding water to trimethylaluminum. The produced aluminoxane oligomer compound may be linear, cyclic, cage, or a mixture thereof.

The organic aluminoxane may be selected from the group consisting of alkylaluminoxane, for example, methylaluminoxane (MAO), ethylaluminoxane (EAO), tetraisobutylaluminoxane (TIBAO), and isobutylaluminoxane (IBAO), and also modified alkylaluminoxane, for example, modified methylaluminoxane (MMAO). The modified methylaluminoxane (manufactured by Akzo Nobel N.V.) includes a hybrid alkyl group such as isobutyl or n-octyl groups in addition to a methyl group.

As a specific example, the organic aluminoxane may be one or a mixture two or more selected from the group consisting of methylaluminoxane (MAO), modified methylaluminoxane (MMAO), ethylaluminoxane (EAO), tetraisobutylaluminoxane (TIBAO), and isobutylaluminoxane (IBAO).

The organic boron compound as the cocatalyst may be boroxine, $NaBH_4$, triethylborane, triphenylborane, triphenylborane ammonia complex, tributylborate, triisopropylborate, tris(pentafluorophenyl)borane, triethyl(tetrapentafluorophenyl)borate, dimethylphenylammonium (tetrapentafluorophenyl)borate, diethylphenylammonium (tetrapentafluorophenyl)borate, methyldiphenylammonium (tetrapentafluorophenyl)borate, or ethyldiphenylammonium (tetrapentafluorophenyl)borate, and the organic boron compound thereof may be mixed with the organic aluminum compound.

Preferably, the cocatalyst may be one or a mixture of two or more selected from the group consisting of methylaluminoxane (MAO), modified methylaluminoxane (MMAO), ethylaluminoxane (EAO), tetraisobutylaluminoxane (TIBAO), isobutylaluminoxane (IBAO), trimethylaluminum (TMA), triethylaluminum (TEA), triisobutylaluminum (TIBA), tri-n-octylaluminum, methylaluminumdichloride, ethylaluminum dichloride, dimethylaluminum chloride, diethylaluminum chloride, aluminumisopropoxide, ethylaluminum sesquichloride, and methylaluminum sesquichloride, preferably methylaluminoxane (MAO) or modified methylaluminoxane (MMAO), and a ratio of the oligomerization catalyst and the cocatalyst may be 1:1 to 10,000:1, preferably 1:1 to 2,000:1, as a mole ratio of the metal of the cocatalyst:transition metal of the oligomerization catalyst.

The oligomerization catalyst composition according to the present invention may further include other possible components in addition to the oligomerization catalyst and the cocatalyst, as long as the component does not impair the nature of the present invention.

In addition, the method for preparing an oligomer according to an exemplary embodiment of the present invention includes introducing an oligomerization catalyst to a reactor, introducing an olefin to the reactor, and reacting the olefin with the oligomerization catalyst to perform oligomerization.

The method for preparing an oligomer according to an exemplary embodiment of the present invention may further include introducing a cocatalyst containing a metal in an amount of 100 to 5000 times the moles of the transition metal to the reactor, wherein the cocatalyst is as described above.

The oligomerization catalyst and the additive which are separate components of the olefin oligomerization catalyst composition disclosed in the present invention are blended at the same time or sequentially in an optional order in the presence of a solvent to provide an olefin oligomerization catalyst composition. Mixing of each component of the catalyst component may be performed at a temperature of −20 to 250° C. and while the catalyst components are mixed, the presence of the olefin may generally represent a protection effect to provide improved catalyst performance. A more preferred temperature range is 45 to 100° C.

An oligomer prepared from the olefin which is a reaction product disclosed in the present invention, in particular, 1-hexene or 1-octene, may be prepared by a heterogeneous liquid phase reaction, a two-phase liquid/liquid reaction, or a bulk phase reaction or a gas phase reaction in which a product olefin acts as a main medium, in the presence of an inert solvent, using the oligomerization catalyst of an olefin, particularly ethylene according to the present invention, a common apparatus, and a contact technique.

The method for preparing an oligomer according to an exemplary embodiment of the present invention may be performed in an inert solvent. That is, the oligomerization catalyst, the cocatalyst, and an optional inert solvent which does not react with an additive may be used, and the inert solvent may be an aliphatic hydrocarbon. The aliphatic hydrocarbon is a saturated aliphatic hydrocarbon, and may include a linear saturated aliphatic hydrocarbon represented by $C_nH_{2n+2}$ (wherein n is an integer of 1 to 15), an alicyclic saturated aliphatic hydrocarbon represented by $C_mH_{2m}$ (wherein m is an integer of 3 to 8), and a saturated aliphatic hydrocarbon in which one or two or more lower alkyl groups having 1 to 3 carbon atoms are substituted. A specific list thereof is as follows: one or more selected from the group consisting of pentane, hexane, heptane, octane, nonene, decane, undecane, dodecane, tetradecane, 2,2-dimethylpentane, 2,3-dimethylpentane, 2,4-dimethylpentane, 3,3-dimethylpentane, 2,2,4-trimethylpentane, 2,3,4-trimethylpentane, 2-methylhexane, 3-methylhexane, 2,2-dimethylhexane, 2,4-dimethylhexane, 2,5-dimethylhexane, 3,4-dimethyhexane, 2-methylheptane, 4-methylheptane, cyclohexane, methylcyclohexane, ethylcyclohexane, isopropylcyclohexane, 1,4-dimethylcyclohexane, and 1,2,4-trimethylcyclohexane, but not limited thereto.

In the method for preparing an oligomer according to an exemplary embodiment of the present invention, the oligomerization reaction may be performed at a temperature of 0 to 200° C., preferably 15 to 130° C., and more preferably 45 to 100° C., under a reaction pressure of an atmospheric pressure to 100 bar, preferably an atmospheric pressure to 80 bar, and more preferably an atmospheric pressure to 60 bar.

In an exemplary embodiment of the present invention, under the oligomerization reaction condition, as an example, a yield of 1-hexene from ethylene may be 10% by mass or more, preferably 30% by mass or more. In this case, the yield refers to grams of 1-hexene formed per 100 g of total C6 products.

In an exemplary embodiment of the present invention, under the oligomerization reaction condition, as an example, a yield of 1-octene from ethylene may be 40% by mass or more, preferably 60% by mass or more. In this case, the yield refers to grams of 1-octene formed per 100 g of total C8 products.

It is recognized therefrom that the method for preparing an oligomer of the present invention uses the oligomer catalyst composition including the heteroatom ligand containing silsesquioxane of the present invention, whereby activity of the catalyst is maintained even at a high temperature, and a produced amount of 1-octene is significantly high, unlike the conventional method.

In the method for preparing an oligomer according to an exemplary embodiment of the present invention, the olefin may be ethylene, and the oligomer may be 1-hexene, 1-octene, or a mixture thereof.

The method for preparing an oligomer according to an exemplary embodiment of the present invention may be performed in a plant including an optional type of reactor. Examples of the reactor include a batch reactor, a semi-bath reactor, and a continuous reactor, but are not limited thereto. The plant may include a reactor, an olefin reactor and an inlet of a catalyst composition in the reactor, a line for flowing out an oligomerization reaction product from the reactor, and at least one separator for separating the oligomerization reaction product in combination, in which the catalyst composition is the oligomerization catalyst composition disclosed in the present invention and may include an oligomerization catalyst having a transition metal coordinated with an organic ligand and a heteroatom ligand, a cocatalyst, and an additive.

The method for preparing an oligomer according to an exemplary embodiment of the present invention improves the problems raised in the process, thereby easily producing 1-hexene, 1-octene, or a mixture thereof.

The following Examples specifically describe the effect of the present invention. However, the following Examples are only illustrative of the present invention, and do not limit the scope of the present invention.

[Ligand Preparation Example 1] Preparation of (phenyl)$_2$PN (propylisobutyl polyhedral oligomeric silsesquioxane)P(phenyl)$_2$ Preparation of Aminopropylisobutyl Polyhedral Oligomeric Silsesquioxane

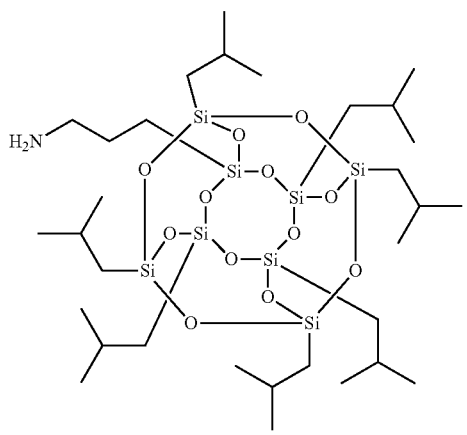 [SMILES: CC(C)C[Si]12O[Si]3(CCCN)O[Si]4(CC(C)C)O[Si](CC(C)C)(O1)O[Si]1(CC(C)C)O[Si](CC(C)C)(O2)O[Si](CC(C)C)(O3)O[Si](CC(C)C)(O4)O1]

Trisilanol silsesquioxane (4.52 g, 5.7 mmol, Sigma-Aldrich Corporation) was dissolved in anhydrous THF (40 ml) in a dried 100 ml flask under a nitrogen atmosphere, and (3-aminopropyl)triethoxysilane (1.6 ml, 7.2 mmol, Sigma-Aldrich Corporation) was added thereto. The mixture was reacted at room temperature for 48 hours or more, a volatile material was removed under a reduced pressure, and the residue was washed with acetonitrile (2×20 ml) to obtain 4.1 g (82%) of an aminopropylisobutyl polyhedral oligomeric silsesquioxane product as a white solid.

$^1$H NMR (500 MHz, CDCl$_3$): δ 2.69 (t, 2H, J=7 Hz, —CH$_2$NH$_2$ tether), 1.85 (m, 7H, CH), 1.54 (m, 2H, CH$_2$ tether), 1.36 (s, 2H, NH$_2$), 0.95 (m, 42H, CH$_3$), 0.60 (m, 2H, Si—CH$_2$ tether, 14H, Si—CH$_2$).

$^{13}$C NMR (600 MHz, CDCl$_3$): δ 44.7, 27.1, 25.7, 23.9, 22.5, 9.2.

FT-ICR MS: m/z [M+H]$^+$ calcd for C$_{31}$H$_{71}$NO$_{12}$Si$_8$: 874.5789; found: 874.3172.

Preparation of (phenyl)$_2$PN(propylisobutyl polyhedral oligomeric silsesquioxane)P(phenyl)$_2$

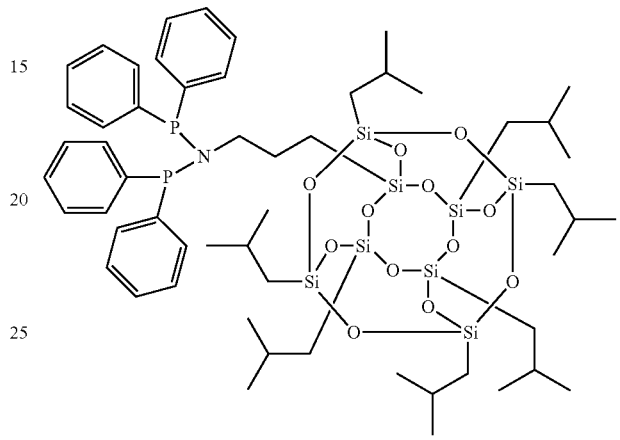

Aminopropylisobutyl polyhedral oligomeric silsesquioxane (0.2 g, 0.23 mmol) was dissolved in dichloromethane (3 ml) in a 20 ml vial under a nitrogen atmosphere, triethylamine (0.13 ml, 0.96 mmol) was mixed therewith, and chlorodiphenylphosphine (0.106 g, 0.48 mmol) was added thereto. The mixture was stirred at room temperature for one hour, a volatile material was removed under reduced pressure, the residue was reslurried and washed with methanol (2×2 ml) and then filtered to obtain 0.21 g (77%) of (phenyl)$_2$PN(propylisobutyl polyhedral oligomeric silsesquioxane)P(phenyl)$_2$ as a white solid product.

$^1$H NMR (500 MHz, CDCl3) δ: 7.36 (br, 8H, aromatics), 7.28 (br, 12H, aromatics), 3.16 (m, 2H, —CH2—), 1.82 (m, 7H, CH), 1.41 (t, 2H, J=6 Hz, —CH2N), 0.90 (m, 42H, CH3), 0.58 (m, 14H, Si—CH2), 0.38 (t, 2H, J=8 Hz, Si—CH2).

$^{13}$C NMR (600 MHz, CDCl3) δ: 139.9, 132.5, 128.5, 127.9, 45.8, 25.7, 24.2, 23.8, 22.5, 9.2.

$^{31}$P NMR (500 MHz, CDCl3) δ: 62.1.

FT-ICR MS: m/z [M+H]$^+$ calcd for C$_{55}$H$_{89}$NO$_{12}$P$_2$Si$_8$: 1242.9262; found: 1242.4033.

[Example 1] Ethylene oligomerization reaction using pentane, and Cr(III)Cl$_3$(tetrahydrofuran)$_3$, (phenyl)2PN(propylisobutyl polyhedral oligomeric silsesquioxane)P(phenyl)2, and mMAO-3A at 45° C.

A 50 ml autoclave reactor was washed with nitrogen under vacuum, 20 ml of pentane was added, and 0.5 ml (0.94 mmol) of mMAO-3A (7 wt %-Al) commercially available from Akzo Nobel N.V. was added thereto. 7.0 mg (20 umol) of Cr(III)Cl$_3$(tetrahydrofuran)$_3$ and 28.8 mg (20 umol) of (phenyl)$_2$PN (propylisobutyl polyhedral oligomeric silsesquioxane)P(phenyl)$_2$ of Ligand Preparation Example 1 in 1 ml of dichloromethane were mixed in a glove box and stirred at room temperature for 5 minutes. A volatile material was removed by drying under reduced pressure, 10 ml of methylcyclohexane was added to dissolve the residue completely, and 0.5 ml (1 umol) of an aliquot was introduced to the reactor. A pressure reactor was filled with 30 bar of ethylene and stirring was performed at a stirring speed of 600 rpm. After 15 minutes, supply of ethylene to the reactor was stopped, stirring was stopped to stop the reaction, and the reactor was cooled to 10° C. or lower. An excess amount of ethylene in the reactor was discharged, and 1.5 ml of 2-ethylhexane was injected to the reactor. A small amount of organic layer sample was passed through a micron syringe filter, and was analyzed with GC-FID. The remaining organic layer was filtered and a solid wax/polymer product was separated. These solid products were dried in an oven at 100° C. overnight, and the resultant product was recorded. A product distribution in this example is summarized in the following Table 1.

[Example 2] Ethylene Oligomerization Reaction Using Hexane, and Cr(III)Cl$_3$(tetrahydrofuran)$_3$, (phenyl)$_2$PN(propylisobutyl polyhedral oligomeric silsesquioxane)P(phenyl)$_2$, and mMAO-3A at 45° C.

An oligomerization reaction was performed in the same manner as in Example 1, except that hexane was used as a reaction solvent. A product distribution in this example is summarized in the following Table 1.

[Example 3] Ethylene Oligomerization Reaction Using Cyclohexane, and Cr(III)Cl$_3$(tetrahydrofuran)$_3$, (phenyl)$_2$PN (propylisobutyl polyhedral oligomeric silsesquioxane)P(phenyl)$_2$, and mMAO-3A at 45° C.

An oligomerization reaction was performed in the same manner as in Example 1, except that cyclohexanone was used as a reaction solvent. A product distribution in this example is summarized in the following Table 1.

[Example 4] Ethylene Oligomerization Reaction Using methylcyclohexane, and Cr(III)Cl$_3$(tetrahydrofuran)$_3$, (phenyl)$_2$PN (propylisobutyl polyhedral oligomeric silsesquioxane)P(phenyl)$_2$, and mMAO-3A at 45° C.

An oligomerization reaction was performed in the same manner as in Example 1, except that cyclohexanone was used as a reaction solvent. A product distribution in this example is summarized in the following Table 1.

[Example 5] Ethylene Oligomerization Reaction Using Methylcyclohexane, and Cr(III)Cl$_3$(tetrahydrofuran)$_3$, (phenyl)$_2$PN (propylisobutyl polyhedral oligomeric silsesquioxane)P(phenyl)$_2$, and mMAO-3A at 60° C.

An oligomerization reaction was performed in the same manner as in Example 1, except that methylcyclohexane was used as a reaction solvent and a reaction temperature was 60° C. A product distribution in this example is summarized in the following Table 1.

[Example 6] Ethylene Oligomerization Reaction Using Methylcyclohexane, and Cr(III)Cl$_3$(tetrahydrofuran)$_3$, (phenyl)$_2$PN(propylisobutyl polyhedral oligomeric silsesquioxane)P(phenyl)$_2$, and mMAO-3A at 80° C.

An oligomerization reaction was performed in the same manner as in Example 1, except that methylcyclohexane was used as a reaction solvent and a reaction temperature was 80° C. A product distribution in this example is summarized in the following Table 1.

[Example 7] Ethylene Oligomerization Reaction Using Methylcyclohexane, and Cr(III)Cl$_3$(tetrahydrofuran)$_3$, (phenyl)$_2$PN (propylisobutyl polyhedral oligomeric silsesquioxane)P(phenyl)$_2$, and mMAO-3A at 100° C.

An oligomerization reaction was performed in the same manner as in Example 1, except that methylcyclohexane was used as a reaction solvent and a reaction temperature was 100° C. A product distribution in this example is summarized in the following Table 1.

[Comparative Ligand Preparation Example 1] Preparation of (phenyl)$_2$PN (n-butyl)P(phenyl)$_2$

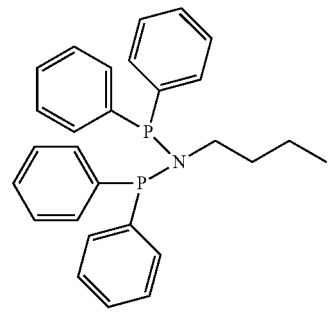 [SMILES: CCCCN(P(c1ccccc1)c1ccccc1)P(c1ccccc1)c1ccccc1]

N-butyl amine (0.3 g, 4.1 mmol) was dissolved in dichloromethane (20 ml) in a 20 ml vial dried under a nitrogen atmosphere, triethylamine (3.51 ml, 25.2 mmol) was mixed therewith, and chlorodiphenylphosphine (1.855 g, 8.4 mmol) was added thereto. The mixture was stirred at room temperature for one hour, a volatile material was removed under reduced pressure, the residue was reslurried and washed with methanol (2×2 ml) and then filtered to obtain 1.22 g (67%) of (phenyl)$_2$PN(n-butyl)P(phenyl)$_2$ as a white solid product.

$^1$H NMR (CDCl$_3$): δ 0.60 (t, 3H, J=7 Hz, CH$_3$), 0.92 (t, 2H, J=7, CH$_2$), 1.07 (m, 2H, CH2), 3.23 (q, 2H, J=9, N—CH$_2$), 7.31 (s, 12H, aromatics), 7.39 (s, 8H, aromatics)

[Comparative Example 1] Ethylene Oligomerization Reaction Using Pentane, and Cr(III)Cl$_3$(tetrahydrofuran)$_3$, (phenyl)$_2$PN(n-butyl)P(phenyl)$_2$, and mMAO-3A at 45° C.

An oligomerization reaction was performed in the same manner as in Example 1, except that (phenyl)$_2$PN(n-butyl)P(phenyl)$_2$ was used as a ligand. A product distribution in this example is summarized in the following Table 1.

[Comparative Example 2] Ethylene Oligomerization Reaction Using Hexane, and Cr(III)Cl$_3$(tetrahydrofuran)$_3$, (phenyl)$_2$PN(n-butyl)P(phenyl)$_2$, and mMAO-3A at 45° C.

An oligomerization reaction was performed in the same manner as in Comparative Example 1, except that hexane was used as a reaction solvent. A product distribution in this example is summarized in the following Table 1.

[Comparative Example 3] Ethylene Oligomerization Reaction Using Cyclohexane, and Cr(III)Cl$_3$(tetrahydrofuran)$_3$, (phenyl)$_2$PN(n-butyl)P(phenyl)$_2$, and mMAO-3A at 45° C.

An oligomerization reaction was performed in the same manner as in Comparative Example 1, except that cyclohexanone was used as a reaction solvent. A product distribution in this example is summarized in the following Table 1.

[Comparative Example 4] Ethylene Oligomerization Reaction Using Methylcyclohexane, and Cr(III)Cl$_3$(tetrahydrofuran)$_3$, (phenyl)$_2$PN(n-butyl)P(phenyl)$_2$, and mMAO-3A at 45° C.

An oligomerization reaction was performed in the same manner as in Comparative Example 1, except that methylcyclohexanone was used as a reaction solvent. A product distribution in this example is summarized in the following Table 1.

[Comparative Example 5] Ethylene Oligomerization Reaction Using Methylcyclohexane, and Cr(III)Cl$_3$(tetrahydrofuran)$_3$, (phenyl)$_2$PN(n-butyl)P(phenyl)$_2$, and mMAO-3A at 60° C.

An oligomerization reaction was performed in the same manner as in Comparative Example 1, except that methylcyclohexane was used as a reaction solvent and a reaction temperature was 60° C. A product distribution in this example is summarized in the following Table 1.

[Comparative Example 6] Ethylene Oligomerization Reaction Using Methylcyclohexane, and Cr(III)Cl$_3$(tetrahydrofuran)$_3$, (phenyl)$_2$PN(n-butyl)P(phenyl)$_2$, and mMAO-3A at 80° C.

An oligomerization reaction was performed in the same manner as in Comparative Example 1, except that methylcyclohexane was used as a reaction solvent and a reaction temperature was 80° C. A product distribution in this example is summarized in the following Table 1.

[Comparative Example 7] Ethylene Oligomerization Reaction Using Methylcyclohexane, and Cr(III)Cl$_3$(tetrahydrofuran)$_3$, (phenyl)$_2$PN(n-butyl)P(phenyl)$_2$, and mMAO-3A at 100° C.

An oligomerization reaction was performed in the same manner as in Comparative Example 1, except that methylcyclohexane was used as a reaction solvent and a reaction temperature was 100° C. A product distribution in this example is summarized in the following Table 1.

TABLE 1

| Catalyst | Activity (kg/gCR/h) | Reaction temperature (° C.) | C6 (wt %) | 1-Hexene in C6 (wt %) | C8 (wt %) | 1-Octene in C8 (wt %) | C10-C14 (wt %) | Polymer (wt %) | Octene/hexene (g ratio) |
|---|---|---|---|---|---|---|---|---|---|
| Example 1 | 1150 | 45 | 21.1 | 39.1 | 63.9 | 96.9 | 10.9 | 4.1 | 3.0 |
| Comparative Example 1 | 125 | 45 | 20.2 | 45.9 | 69.8 | 97.2 | 8.8 | 1.2 | 3.5 |
| Example 2 | 870 | 45 | 21.7 | 34.3 | 63.3 | 95.7 | 10.2 | 4.8 | 2.9 |
| Comparative Example 2 | 166 | 45 | 19.2 | 51.3 | 69.3 | 96.1 | 9.9 | 1.6 | 3.6 |
| Example 3 | 981 | 45 | 22.0 | 36.4 | 64.3 | 95.2 | 9.8 | 4.0 | 2.9 |
| Comparative Example 3 | 214 | 45 | 11.5 | 30.5 | 71.5 | 95.8 | 15.8 | 1.2 | 6.2 |
| Example 4 | 1049 | 45 | 23.4 | 41.9 | 62.7 | 95.4 | 10.3 | 3.6 | 2.7 |
| Comparative Example 4 | 446 | 45 | 13.1 | 34.2 | 70.8 | 96.5 | 15.9 | 0.2 | 5.4 |
| Example 5 | 997 | 60 | 24.8 | 47.4 | 64.1 | 95.7 | 9.0 | 2.0 | 2.6 |
| Comparative Example 5 | 575 | 60 | 23.0 | 51.7 | 68.6 | 97.0 | 7.6 | 0.8 | 3.0 |
| Example 6 | 873 | 80 | 26.4 | 53.7 | 63.5 | 96.6 | 8.1 | 2.0 | 2.4 |
| Comparative Example 6 | 388 | 80 | 18.1 | 67.7 | 65.8 | 97.6 | 16.1 | 0.1 | 3.6 |
| Example 7 | 640 | 100 | 30.7 | 63.7 | 59.9 | 96.9 | 7.7 | 1.7 | 2.0 |
| Comparative Example 7 | 239 | 100 | 29.0 | 67.6 | 61.8 | 97.2 | 7.7 | 1.6 | 2.1 |

As seen from Table 1, it is recognized that the oligomerization catalyst composition including the heteroatom ligand having silsesquioxane of the present invention has excellent activity as compared with those of the Comparative Examples, and in particular, maintains activity even at a high polymerization temperature.

The heteroatom ligand according to an exemplary embodiment of the present invention is a heteroatom ligand having a silsesquioxane derivative and is coordinated with a transition metal including an organic ligand, whereby solubility is extremely excellent unlike the conventional art, and allows use of various polymerization solvents the time oligomerization of olefins, whereby a range of production process application is very wide and mass production is possible, solubility is excellent while a catalyst activity is maintained even at a high temperature, tube blockage and fouling are absent due to less production of byproducts, and shut down for removing the byproducts is not required so as to be very economical.

Besides, the oligomerization catalyst according to an exemplary embodiment of the present invention has excellent catalyst activity even at a high temperature, so that the oligomer may be prepared in the oligomerization process of olefins even with a small amount of catalyst and a small amount of cocatalyst.

Furthermore, the oligomerization catalyst according to an exemplary embodiment of the present invention does not have reduced activity even at a high temperature and has excellent selectivity, so that 1-hexene or 1-octene, in particular, 1-octene, may be prepared with high selectivity from olefin, in particular ethylene.

The invention claimed is:

1. A heteroatom ligand represented by the following Chemical Formula 1:

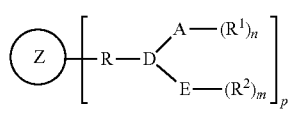

[Chemical Formula 1]

wherein

A and E are independently of each other selected from the group consisting of phosphorus, arsenic, antimony, oxygen, bismuth, sulfur, selenium, and nitrogen, D is a linking group between A and E, Z is a silsesquioxane derivative, R is hydrocarbylene, $R_1$ and $R_2$ are independently of each other substituted or unsubstituted hydrocarbyl or substituted or unsubstituted heterohydrocarbyl, p is an integer of 1 to 18, and n and m are independently of each other determined by each valency or oxidation state of A or E.

2. The heteroatom ligand of claim 1, wherein the silsesquioxane derivative is represented by the following Chemical Formula 2:

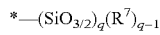

[Chemical Formula 2]

wherein $R^7$ is hydrogen, hydroxy, a halogen, hydrocarbyl, substituted hydrocarbyl, heterohydrocarbyl, or substituted heterohydrocarbyl, and q is 2, 4, 6, 8, 10, 12, 14, 16, or 18.

3. The heteroatom ligand of claim 2, wherein $R^7$ is C1-C10alkyl.

4. The heteroatom ligand of claim 2, wherein in Chemical Formula 2, q is 8.

5. The heteroatom ligand of claim 1, wherein D is any one selected from the group consisting of organic linking groups including substituted or unsubstituted hydrocarbylene or substituted or unsubstituted heterohydrocarbylene; and inorganic linking groups including a single atomic link.

6. The heteroatom ligand of claim 1, wherein the heteroatom ligand is selected from the following Chemical Formulae 3 to 5:

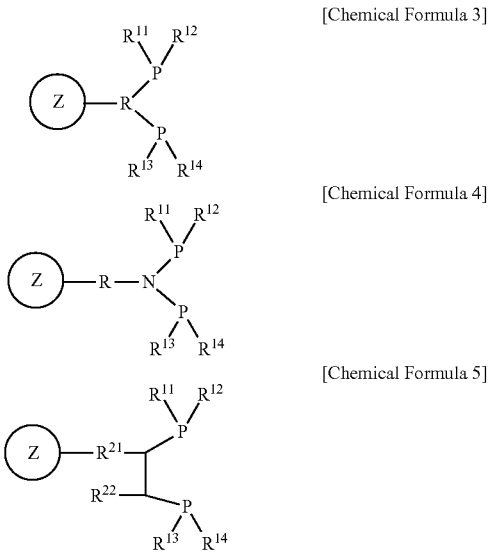

[Chemical Formula 3]

[Chemical Formula 4]

[Chemical Formula 5]

wherein

Z is a silsesquioxane derivative, $R^{11}$ to $R^{14}$ are independently of one another hydrocarbyl, substituted hydrocarbyl, heterohydrocarbyl, or substituted heterohydrocarbyl, R and $R^{21}$ are independently of each other substituted or unsubstituted C6-C20arylene, substituted or unsubstituted C6-C20aryleneC1-C10alkylene, substituted or unsubstituted C6-C20aryleneC2-C10alkenylene, substituted or unsubstituted C6-C20aryleneC2-C10alkynylene, substituted or unsubstituted C1-C10alkylene, substituted or unsubstituted C2-C10alkenylene, substituted or unsubstituted C2-C10alkynylene, or substituted or unsubstituted C3-C20heteroarylene, and $R^{22}$ is substituted or unsubstituted C1-C20aryl, substituted or unsubstituted C6-C20arylC1-C10alkyl, substituted or unsubstituted C6-C20arylC2-C10alkenyl, substituted or unsubstituted C6-C20arylC2-C10alkynyl, C1-C10alkyl, C2-C10alkenyl, substituted or unsubstituted C2-C10alkynyl, substituted or unsubstituted C3-20heteroaryl, or

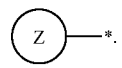

7. The heteroatom ligand of claim 6, wherein
in Chemical Formulae 3 to 5, $R^{11}$ to $R^{14}$ are independently of one another substituted or unsubstituted C6-C20aryl, substituted or unsubstituted C6-C20arylC1-C10alkyl, substituted or unsubstituted C6-C20arylC2-C10alkenyl, or substituted or unsubstituted C6-C20arylC2-C10alkynyl, R and $R^{21}$ are independently of each other C1-C10alkylene, and $R^{22}$ is C1-C10alkyl or

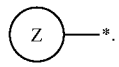

8. The heteroatom ligand of claim 6, wherein the silsesquioxane derivative is $*-(SiO_{3/2})_q(R^7)_{q-1}$, wherein $R^7$ is hydrocarbyl, substituted hydrocarbyl, heterohydrocarbyl, or substituted heterohydrocarbyl, and q is 2, 4, 6, 8, 10, 12, 14, 16, or 18.

9. The heteroatom ligand of claim 7, wherein $R^{11}$ to $R^{14}$ are independently of one another C6-C20aryl substituted by any one or more selected from the group consisting of halogens, C1-C10alkyl, haloC1-C10alkyl, C2-C10alkenyl, C2-C10alkynyl, C1-C10alkoxy, and haloC1-C10alkoxy.

10. An oligomerization catalyst comprising: the heteroatom ligand of claim 1 and a transition metal.

11. A method for preparing an oligomer, the method comprising:
  introducing the oligomerization catalyst of claim 10 to a reactor;
  introducing an olefin to the reactor; and
  reacting the olefin with the oligomerization catalyst to be oligomerized.

12. The method for preparing an oligomer of claim 11, wherein the olefin is ethylene, and the oligomer is 1-hexene or 1-octene.

13. The method for preparing an oligomer of claim 11, further comprising: introducing a cocatalyst containing a metal in an amount of 100 to 5,000 times the moles of the transition metal to the reactor.

14. The method for preparing an oligomer of claim 13, wherein the cocatalyst is an organic aluminum compound, organic aluminoxane, an organic boron compound, an organic salt, or a mixture thereof.

15. The method for preparing an oligomer of claim 14, wherein the cocatalyst is one or a mixture or two or more selected from the group consisting of methylaluminoxane (MAO), modified methylaluminoxane (MMAO), ethylaluminoxane (EAO), tetraisobutylaluminoxane (TIBAO), isobutylaluminoxane (IBAO), trimethylaluminum (TMA), triethylaluminum (TEA), triisobutylaluminum (TIBA), tri-n-octylaluminum, methylaluminumdichloride, ethylaluminum dichloride, dimethylaluminum chloride, diethylaluminum chloride, aluminumisopropoxide, ethylaluminum sesquichloride, and methylaluminum sesquichloride.

* * * * *

UNITED STATES PATENT AND TRADEMARK OFFICE
CERTIFICATE OF CORRECTION

PATENT NO. : 11,020,729 B1
APPLICATION NO. : 16/622055
DATED : June 1, 2021
INVENTOR(S) : Ho Seong Lee et al.

Page 1 of 1

It is certified that error appears in the above-identified patent and that said Letters Patent is hereby corrected as shown below:

On the Title Page

Column 2, Other Publications, Line 2, delete "spherpsilicates:" and insert -- spherosilicates: --

In the Specification

Column 1, Line 12, delete "10-2017/0076510" and insert -- 10-2017-0076510 --

In the Claims

Column 23, Line 51, Claim 1, delete "$R_1$" and insert -- $R^1$ --

Column 23, Line 51, Claim 1, delete "$R_2$" and insert -- $R^2$ --

Column 24, Line 51, Claim 6, delete "C1-C20aryl," and insert -- C6-C20aryl, --

Column 24, Line 57, Claim 6, delete "C3-20heteroaryl," and insert -- C3-C20heteroaryl, --

Signed and Sealed this
Fourth Day of January, 2022

Drew Hirshfeld
*Performing the Functions and Duties of the
Under Secretary of Commerce for Intellectual Property and
Director of the United States Patent and Trademark Office*